US00PP37489P2

(12) United States Plant Patent
Carrella

(10) Patent No.: US PP37,489 P2
(45) Date of Patent: Jun. 23, 2026

(54) ***CALIBRACHOA* PLANT NAMED 'KLECA24A40'**

(50) Latin Name: ***Calibrachoa* sp.**
Varietal Denomination: KLECA24A40

(71) Applicant: KLEMM + SOHN GMBH & CO. KG, Stuttgart (DE)

(72) Inventor: Angelo Carrella, Palma Campania (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/239,702

(22) Filed: Jun. 16, 2025

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC . A01H 5/02; A01H 5/00; A01H 6/821; A01H 6/82
See application file for complete search history.

(56) References Cited

PUBLICATIONS

Ball Seed Minifamous Neo Magenta Star Calibrachoa, retrieved on Sep. 24, 2025 at https://info.ballseed.com/PlantInfo/?phid=066007160031385, 2 pp. (Year: 2025).*
Lawn & Garden Retailer FlowerTrials 2024 set for June 11-14, retrieved on Sep. 24, 2025 at https://lgrmag.com/news/flowertrials-2024-set-for-june-11-14/#:~:text=FlowerTrials%202024%20set%20for%20June,within%20the%20global%20horticultural%20community., 3 pp. (Year: 2024).*
Selecta One Spring Annuals Trixi 2024/2025 retrieved on Sep. 24, 2025 at https://josvainiugeles.It/wp-content/uploads/2024/09/Selecta-Annuals-2025.pdf, introductory pp. 1-3, pp. 2-5, 14-15, 168-173 (8 pp. total). (Year: 2025).*
Selecta One 2024, retrieved on Sep. 29, 2025 at https://selecta-one.com/en/company/news-detail/new-catalogue-spring-annuals-trixi-2024-25, 3 pp. (Year: 2024).*
Van der Ploeg FlowerTrials 2024 continues to be an unmissable open-house event for bedding plant industry (1), retrieved on Sep. 24, 2025 at https://aiph.org/floraculture/news/flowertrials-continues-to-be-an-unmissable-open-house-event-for-bedding-plant-industry-1/, 27 pp. (Year: 2024).*
West Tennessee AgResearch and Education Center, UT Gardens Jackson 2025 retrieved on Sep. 24, 2025 at https://westtn.tennessee.edu/wp-content/uploads/sites/35/2025/04/2025-Spring-Plant-sale-for-distribution-4.pdf, 18 pp. (Year: 2025).*

* cited by examiner

*Primary Examiner* — June Hwu
(74) *Attorney, Agent, or Firm* — Weatherly IP Solutions, LLC; Karen P. Bechtold; James M. Weatherly

(57) ABSTRACT

A new *Calibrachoa* plant particularly distinguished by having a magenta flower color with white stripes, good branching and a semi-mounding habit is disclosed.

1 Drawing Sheet

Genus and species: *Calibrachoa* sp.
Variety denomination: 'KLECA24A40'.

BACKGROUND OF THE NEW PLANT

The present invention comprises a new and distinct variety of *Calibrachoa*, botanically known as *Calibrachoa* sp., and hereinafter referred to by the variety name 'KLECA24A40'. 'KLECA24A40' originated from a controlled-cross between the female *Calibrachoa* variety 'KLECA22822' (unpatented) and the male *Calibrachoa* variety 'KLECA22915' (U.S. Plant Pat. No. 36,002).

In May 2020, the two *Calibrachoa* parental lines were crossed via a controlled-cross in Nairobi, Kenya and seeds were obtained. The seeds were sown and plants were grown for evaluation. A plant line was selected in May 2021 in Stuttgart, Germany and subsequently named 'KLECA24A40'. 'KLECA24A40' was first vegetatively propagated by cuttings in May 2021 in Stuttgart, Germany. 'KLECA24A40' was found to reproduce true to type in successive generations of asexual propagation via cuttings.

SUMMARY

The following are the most outstanding and distinguishing characteristics of this new variety when grown under normal horticultural practices in Stuttgart, Germany.

1. Magenta flower color with white stripes; and
2. Good branching and semi-mounding habit.

DESCRIPTION OF THE PHOTOGRAPH

This new *Calibrachoa* plant is illustrated by the accompanying photograph which shows a close-up of the whole plant. The photograph is of an 11-week-old-plant grown indoors in Stuttgart, Germany in May 2024. The colors shown are as true as can be reasonably obtained by conventional photographic procedures.

DESCRIPTION OF THE NEW VARIETY

The following detailed descriptions set forth the distinctive characteristics of 'KLECA24A40'. The data which define these characteristics were collected from asexual reproductions carried out in Stuttgart, Germany. Data was collected on 14-week old plants after transplant in Latina, Italy. Color references are to The R.H.S. Colour Chart of The Royal Horticultural Society of London (R.H.S.), 5th edition (2007).

Classification:

*Family*.—Solanaceae.

*Species*.—*Calibrachoa* sp.

*Common name*.—*Calibrachoa*.

Parentage:

*Female*.—'KLECA22822' (unpatented).

*Male*.—'KLECA22915' (U.S. Plant Pat. No. 36,002).

Plant description:

*Life cycle*.—Annual.

*Form*.—Short-lived subshrub.

*Habit*.—Semi-trailing.

*Height* (*from soil line to top of foliage*).—9.8 cm.

*Spread*.—49.0 cm.

Propagation:

*Type cuttings*.—Tip cuttings.

*Time to produce a rooted cutting*.—3 weeks.

Stems:

*Stem color*.—RHS 144B.

*Pubescence*.—Present.

*Pubescence color*.—RHS 155A.

*Stem diameter*.—0.1 cm.

*Stem length*.—From soil line to first node: 1.1 cm. Total length: 32.4 cm.

*Internode length*.—2.1 cm.

Leaves:

*Arrangement*.—Alternate.

*Shape*.—Elliptic.

*Apex*.—Acute.

*Base*.—Acute.

*Margin*.—Ciliate.

*Surface pubescence*.—Present.

*Pubescence color*.—RHS 155A.

*Venation color*.—Upper surface: RHS 137A. Lower surface: RHS 137D.

*Venation pattern*.—Arcuate.

*Length*.—3.1 cm (mature leaves).

*Width*.—1.1 cm (mature leaves).

*Color*.—Upper surface: RHS 137A. Lower surface: RHS 137D.

*Fragrance*.—Absent.

Flowers:

*Flowering habit*.—Single flower.

*Flower type*.—Single.

*Flowering requirements*.—A minimum amount of 10.5 to 11 hours per day of sunlight is required.

*Duration of flowers*.—7 to 12 days.

*Corolla*.—Smooth (both upper and lower surfaces).

*Shape*.—Funnel form.

*Corolla lobing*.—Obtuse, medium lobing.

*Fragrance*.—Absent.

*Upper surface flower vein conspicuousness*.—Weak.

Flower buds:

*Surface*.—Pubescent.

*Length*.—2.1 cm.

*Diameter*.—0.35 cm.

*Shape*.—Irregular to oblong.

*Color*.—RHS N78C (top buds) 150D (base buds).

Peduncle:

*Length*.—1.4 cm.

*Diameter*.—*Less than* 0.1 cm.

*Color*.—RHS 144D.

*Texture*.—Pubescent.

*Anthocyanin color*.—RHS 59C (partially present, color shaded).

Flower description:

*Flower depth*.—2.5 cm.

*Flower tube length*.—1.7 cm.

*Flower tube diameter*.—0.8 cm.

*Flower diameter*.—4.3 cm.

Sepals:

*Number of sepals*.—5 per flower.

*Shape*.—Ovate.

*Apex*.—Narrow acute.

*Margin*.—Ciliate.

*Length*.—1.0 cm.

*Diameter*.—0.3 cm.

*Sepal color*.—Upper surface: RHS 138A. Lower surface: RHS 144B.

Petals:

*Number of petals*.—5 per flower.

*Shape*.—Obcordate.

*Length*.—1.9 cm.

*Apex*.—Obcordate.

*Margin*.—Entire.

*Base*.—Fuse in the tube.

*Pubescence*.—Absent on both surfaces.

*Flower lobing*.—Obtuse.

*Lobe length*.—1.9 cm.

*Lobe width*.—1.4 cm.

*Color*.—Lobe color: Upper surface: RHS N74A main color and RHS NN155C colored stripes; main color is medium sized at color transition to corolla tube; narrow stripes along the fused part of the corolla lobe. Lower surface: RHS N78C main color and RHS NN155A colored stripes; main color is medium sized at color transition to corolla tube; narrow stripes along the fused part of the corolla lobes. Corolla tube color: Inner: RHS 12C. Outer: RHS 150D.

*Fragrance*.—Absent.

Reproductive organs:

*Stamen number*.—5.

*Stamen color*.—Anther color: RHS 13B. Filament color: RHS 1C. Pollen color: RHS 12A.

*Ovary*.—Placenta arrangement: Ovate. Pistil number: 1. Pistil length: 0.7 cm. Stigma color: RHS 145B. Style length: 0.6 cm. Style color: RHS 145B.

Fruit/seed set: None observed.

Disease/insect resistance: No pests and disease were observed.

COMPARISON WITH PARENTAL LINES AND KNOWN VARIETY

'KLECA24A40' is distinguished from its parental lines as described in Table 1:

TABLE 1

Comparison with Parental Lines

| Trait | Variety 'KLECA24A40' | Female Parent 'KLECA22822' (unpatented) | Male Parent 'KLECA22915' (U.S. Plant Pat. No. 36,002) |
|---|---|---|---|
| Main Flower Color | Magenta | Blue | Red |

'KLECA24A40' is most similar to the *Calibrachoa* plant named 'KLECA16006' (U.S. Plant Pat. No. 29,433). Differences between the two varieties are described in Table 2:

TABLE 2

Comparison with Similar Variety

| Trait | Variety 'KLECA24A40' | Commercial line 'KLECA16006' |
|---|---|---|
| Main Flower Color | Magenta | Pink |

I claim:

1. A new and distinct variety of *Calibrachoa* plant designated 'KLECA24A40' as illustrated and described herein.

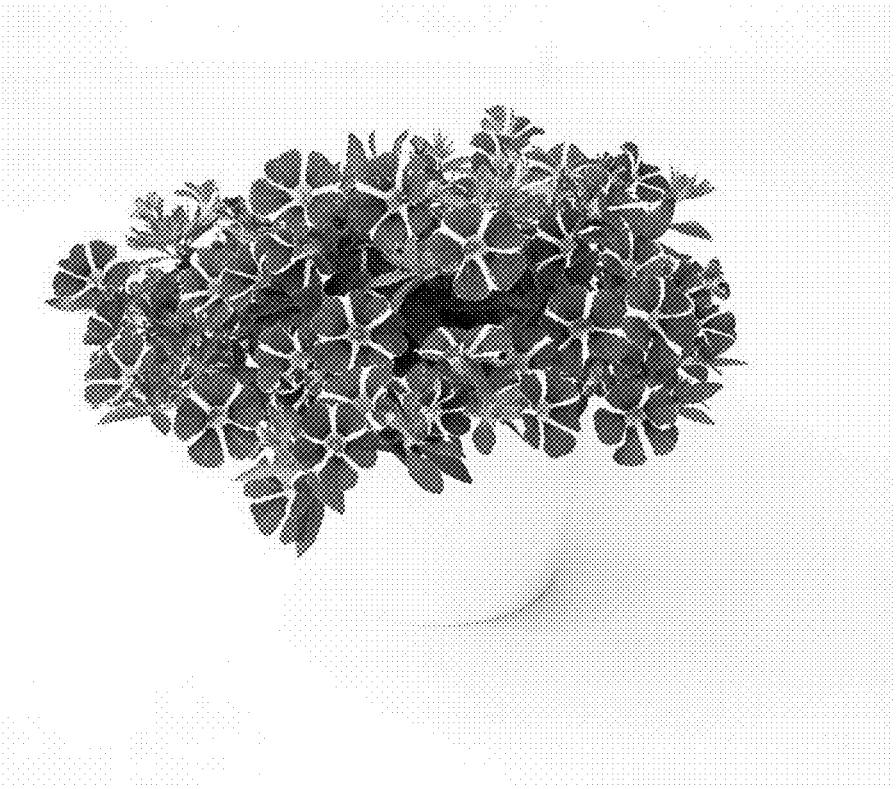

* * * * *